United States Patent
Boege et al.

(10) Patent No.: US 7,295,316 B2
(45) Date of Patent: Nov. 13, 2007

(54) FLUORESCENT DETECTOR WITH AUTOMATIC CHANGING FILTERS

(75) Inventors: Steven J. Boege, San Mateo, CA (US);
Jon A. Hoshizaki, Cupertino, CA (US);
Mark F. Oldham, Los Gatos, CA (US);
Liana Ilkova, Sunnyvale, CA (US)

(73) Assignee: Applera Corporation, Foster City, CA (US)

(*) Notice: Subject to any disclaimer, the term of this patent is extended or adjusted under 35 U.S.C. 154(b) by 450 days.

(21) Appl. No.: 10/758,667

(22) Filed: Jan. 14, 2004

(65) Prior Publication Data
US 2005/0151972 A1  Jul. 14, 2005

(51) Int. Cl.
*G01N 21/25* (2006.01)
(52) U.S. Cl. .................................. 356/417
(58) Field of Classification Search .............. 356/417, 356/418; 250/458.1, 461.2
See application file for complete search history.

(56) References Cited

U.S. PATENT DOCUMENTS

| 4,972,258 | A | 11/1990 | Wolf et al. |
| 5,943,129 | A * | 8/1999 | Hoyt et al. .............. 356/318 |
| 6,225,636 | B1 | 5/2001 | Ginestet |
| 6,320,660 | B1 * | 11/2001 | Ju et al. .................. 356/417 |
| 6,333,501 | B1 * | 12/2001 | Labrenz ............... 250/341.5 |
| 6,518,068 | B1 * | 2/2003 | Gambini et al. ........... 436/50 |
| 6,534,308 | B1 | 3/2003 | Palsson et al. |
| 6,633,662 | B2 | 10/2003 | Ravkin |
| 6,829,051 | B2 * | 12/2004 | Abe et al. ................ 356/417 |
| 7,050,224 | B2 * | 5/2006 | Kawamata et al. ........ 359/359 |
| 2003/0011772 | A1 * | 1/2003 | Abe et al. ................. 356/417 |
| 2003/0148505 | A1 | 8/2003 | Gambini et al. |
| 2004/0066510 | A1 | 4/2004 | Hoff et al. |
| 2004/0072335 | A1 * | 4/2004 | Boege et al. ........... 435/287.2 |

FOREIGN PATENT DOCUMENTS

| EP | 0 987 540 A2 | 3/2000 |
| EP | 1 411 345 A1 | 4/2004 |
| JP | 10 221242 A | 8/1998 |
| JP | 2001 083090 A | 3/2001 |
| JP | 2002 014044 A | 1/2002 |
| WO | WO 99/60381 | 11/1999 |
| WO | WO 01/07896 A1 | 2/2001 |

OTHER PUBLICATIONS

International Search Report from Int'l Application No. PCT/US2005/001485, mailing date of Aug. 29, 2005; along with Written Opinion of ISA.
"Fluorescence Microscopy Reflected Light," http://micro.magnet.fsu.edu/primer/techniques/fluorescence/reflectlightpaths.html.
Lee et al., "Seven-Color, Homogeneous Detection of Six PCR Products," Research Report, BioTechniqes, vol. 27, No. 2 (1999) pp. 342-349.

* cited by examiner

*Primary Examiner*—Roy M. Punnoose

(57) ABSTRACT

A fluorometry device and method adapted to determine concentration of spectrally distinguishable species in a biological sample with a plurality of movable optical devices.

18 Claims, 7 Drawing Sheets

FLUORESCENT DETECTOR WITH AUTOMATIC CHANGING FILTERS

FIELD

The present teaching related to methods and systems for fluorescent detection in biological samples.

INTRODUCTION

Polymerase chain reaction (PCR) is a process for amplifying or multiplying quantities of double-stranded deoxyribonucleic acid (DNA) in a sample. Measurements can be taken, in situ, to monitor the performance of the PCR process. One measurement technique is microscopy. Microscopy can be used to spatially resolve features of interest in the DNA content of the sample based on dyes that fluoresce in the presence of DNA. However, microscopy systems are limited to viewing only one depth of view of the sample at a time, and thus, are unsuitable for making quantitative measurements, such as a concentration measurement. To resolve different features, microscopy systems use collimating lenses to collimate the light reaching the sample and to collimate the light reaching the detector. Collimated light permits information about the spatial content from one depth of field plane to be accurately imaged on the detector. However, microscopy systems are limited to viewing only one depth of field plane at a time.

Another measuring technique is fluorometry. Fluorometry utilizes microvolume fluorometers (spectofluorometers) to spectrally resolve fluorescent light from the volume of biological sample to provide quantitative measurements such as concentration. Fluorometers can illuminate the sample and utilize dyes that fluoresce in the presence of DNA. The fluorescence emitted by a dye can be quantitatively measured using an optical device and a detector without collimating the light through the optical device and without focusing the light from the sample on the detector.

High-throughput systems can provide DNA amplification of multiple samples in parallel, such as in a microwell tray or microcard. Assays can provide multiple DNA target sequences of interest, such as diagnostic assays, for example, HIV screening. These assays can provide multiple spectrally distinguishable species, such as different fluorescent dyes, in each of the multiple samples thermally cycled in parallel. It is desirable to detect multiple types of dyes or low concentrations of dye with optimized optical devices for each spectral range of detection without multiple mechanical and electronic mechanisms and motors that require frequent adjustment and realignment.

SUMMARY

According to various embodiments, the present teaching can provide a fluorometry device for determining concentration of spectrally distinguishable species in a biological sample, the device including a light source adapted to provide a source beam, a plurality of samples, a plurality of optical devices adapted to filter the source beam, to filter fluorescent light from the samples, and to separate the source beam from the fluorescent light, wherein each of the plurality of optical devices is coupled to a movable platform, and a detector adapted to receive the fluorescent light emitted from the samples, wherein the fluorescent light is not in focus and does not provide spatial content from a focus plane in the samples, wherein the device provides a data signal representative of the concentration of spectrally distinguishable species based on the intensity of fluorescent light emitted by the samples.

According to various embodiments, the present teaching can provide a method of determining the concentration of spectrally distinguishable species in a biological sample with fluorometry, the method including moving a movable platform to position a first optical device in the optical paths between a light source and a plurality of samples and between the sample region and a detector, passing light from the light source to the sample region and from the sample region to the detector through a first optical device, wherein the first optical device passes light in a first wavelength band that primarily excites a first dye from the light source to the sample region, and passes light in a second wavelength band that is primarily emitted from the first dye from sample region to the detector, moving the movable platform to position a second optical device in the optical paths between the light source and the sample region and between the sample region and the detector, passing light from the light source to sample region and from the sample region to the detector through the second optical device, wherein the second optical device passes light in a third wavelength band that primarily excites a second dye from the light source to the sample region, and passes light in a fourth wavelength band that is primarily emitted from of the second dye from the sample region to the detector, focusing the light in the second wavelength band and fourth wavelength band on the pupil of the camera, and generating a data signal representative of the concentration of the spectrally distinguishable species in the sample based on the light passed from the sample region to the detector.

According to various embodiments, the present teaching can provide an optical device for fluorometry to determine concentration of spectrally distinguishable species in a biological sample, the device including a first filter to condition excitation light, a second filter to condition emission light, and a beamsplitter to separate the excitation light and the emission light, wherein the optical device is adapted to focus the emission light on the pupil of a detector.

According to various embodiments, the present teaching can provide a method of determining the concentration of spectrally distinguishable species in a biological sample with fluorometry, the method including providing a plurality of samples including a plurality of spectrally distinguishable species, providing a plurality of optical devices adapted to filter excitation light, to filter fluorescent light from the samples, and to separate the excitation light from the fluorescent light, wherein each of the plurality of optical devices is coupled to a movable platform, and wherein each optical device is adapted to one spectrally distinguishable species in the samples, focusing the light in the second wavelength band and fourth wavelength band on the pupil of the camera, thermally cycling the plurality of samples, transitioning between optical device by moving the platform, determining the concentration of each spectrally distinguishable species throughout the thermal cycling.

According to various embodiments, the present teaching can provide an apparatus for determining the concentration of spectrally distinguishable species in a biological sample by fluorometry, the device including means for moving each one of a plurality of optical devices disposed on a platform to receive a source beam directed towards a sample and emitted from a light source, means for blocking a plurality of wavelengths of light in the source beam, means for blocking a plurality of wavelengths of light emitted from the sample when the sample includes DNA and at least one dye, and means for generating a plurality of data signals, each data signal representative of the concentration of DNA in the sample, wherein a data signal is generated when each one of the plurality of optical devices receives the source beam.

It is to be understood that both the foregoing general description and the following detailed description are exemplary and explanatory only and are not restrictive of the invention as claimed.

The accompanying drawings, which are incorporated in and constitute a part of this specification, illustrate some embodiments of the invention, and together with the description serve to explain the principles of the invention.

DESCRIPTION OF VARIOUS EMBODIMENTS

Figure 1:
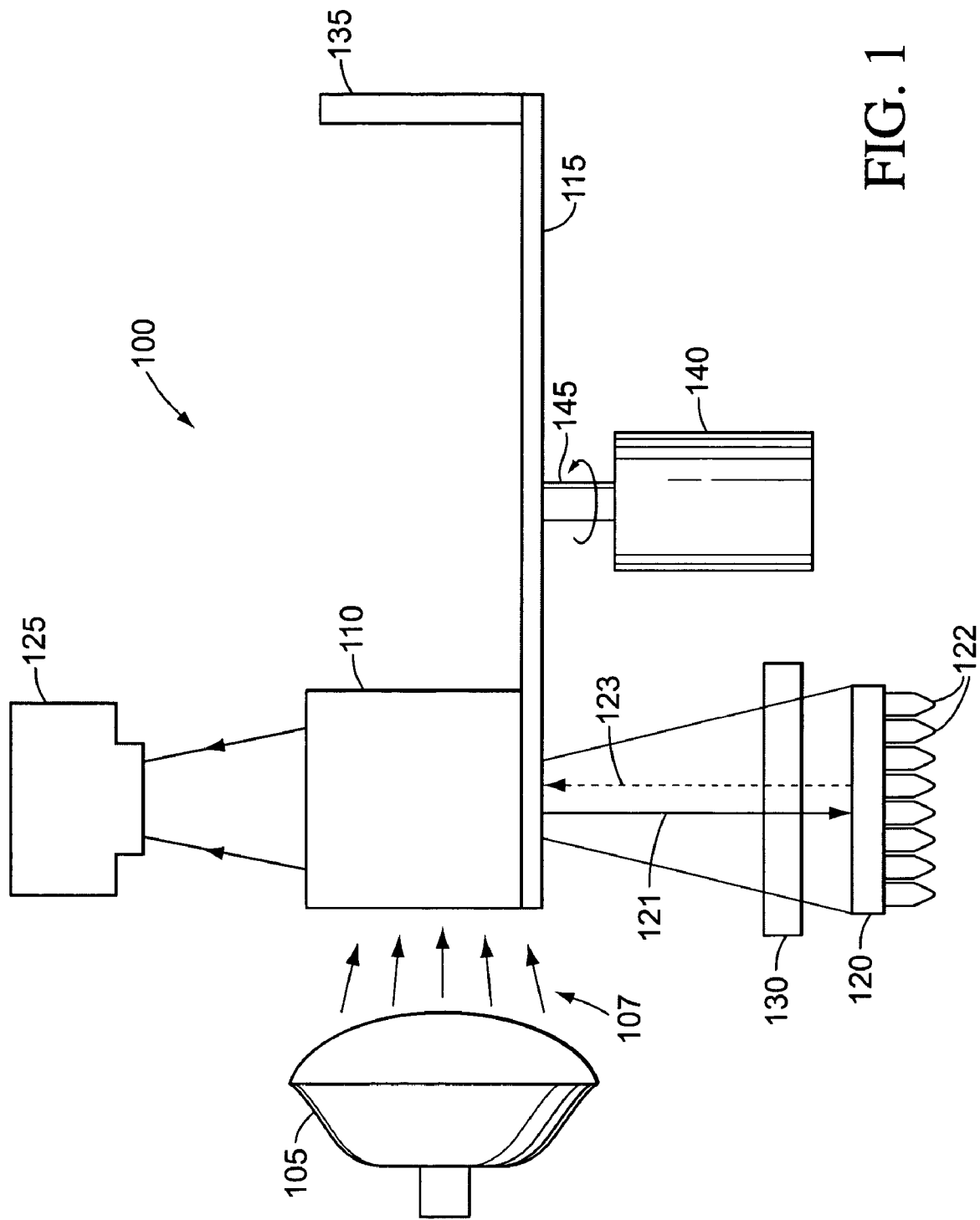
FIG. 1 illustrates a representative fluorometry system according to various embodiments of the present teachings.

Reference will now be made in detail to some embodiments of the invention, examples of which are illustrated in the accompanying drawings. Wherever possible, the same reference numbers will be used throughout the drawings to refer to the same or like parts.

The term "light source" as used herein refers to a source of photons that can provide excitation that results in fluorescent emission. Light sources can include, but are not limited to, white light, halogen lamps, lasers, solid state lasers, laser diodes, micro-wire lasers, diode solid state lasers (DSSL), vertical-cavity surface-emitting lasers (VCSEL), LEDs, phosphor coated LEDs, organic LEDs (OLED), thin-film electroluminescent devices (TFELD), phosphorescent OLEDs (PHOLED), inorganic-organic LEDs, LEDs using quantum dot technology, LED arrays, an ensemble of LEDs, floodlight systems using LEDs, and/or white LEDs, filament lamps, arc lamps, gas lamps, and fluorescent tubes. Light sources can have high radiance, such as lasers, or low radiance, such as LEDs. The different types of LEDs mentioned above can have a medium to high radiance.

The term "detector" as used herein refers to any component, portion thereof, or system of components that can detect light including a charged coupled device (CCD), back-side thin-cooled CCD, front-side illuminated CCD, a CCD array, a photodiode, a photodiode array, a photomultiplier tube (PMT), a PMT array, complimentary metal-oxide semiconductor (CMOS) sensors, CMOS arrays, a charge-injection device (CID), CID arrays, etc. The detector can be adapted to relay information to a data collection device for storage, correlation, and/or manipulation of data, for example, a computer, or other signal processing system.

The term "sample volume" as used herein refers to the sample in any structure that provides containment to the sample. The sample volume can be open or transparent to provide entry to excitation light and exit to fluorescent light. The transparency can be provided by glass, plastic, fused silica, etc. The sample chamber can take any shape including a well, a tube, a vial, a cuvette, a tray, a multi-well tray, a microcard, a microslide, a capillary, an etched channel plate, a molded channel plate, an embossed channel plate, etc. The sample chamber can be part of a combination of multiple sample chambers grouped into a row, an array, an assembly, etc. Multi-chamber arrays can include 12, 24, 36, 48, 96, 192, 384, or more, sample chambers. The sample chamber can be shaped to a multi-well tray under the SBS microtiter format.

The term "sample" as used herein refers to any biological or chemical substance in solution with components that can be excited by excitation light to emit fluorescent light. The sample can include one or more nucleic acid sequences to be amplified and/or sequenced. The sample can include reactants for polymerase chain reaction (PCR) and other reactions such as ligase chain reaction, antibody binding reaction, oligonucleotide ligations assay, and hybridization assay. The sample can be subjected to thermal cycling.

The term "spectrally distinguishable species" as used herein refers to fluorescent dyes can be used to provide different colors that are at least spectrally distinguishable or spectrally distinct. Several dyes will be apparent to one skilled in the art of dye chemistry. One or more colors can be collected to provide identification of the particular dye or dyes detected. The emitter can be a dye-labeled fragment of nucleotides. The dye can be marker triggered by a fragment of nucleotides. The dye can provide identification of components of the sample by association, for example, bonding to or reacting with a detectable marker, for example, a respective dye and quencher pair. The respective identifiable component can be positively identified by the fluorescence of the dye. The dye can be a normally quenched dye, that can become unquenched in the presence of a particular target component in the sample. The fluorescent dyes can be selected to exhibit respective and, for example, different, excitation and emission wavelength ranges. The dye can be measured to quantitate the components. The dye can be detected in real-time to provide information about the identifiable components throughout the reaction. Examples of dye with desirable excitation and emission wavelengths can include 5-FAM™, SYBR Green, TET™, VIC™, JOE, TAMRA, NED, ROX, CY3, Texas Red, CY5, etc. The present teaching apply to red dyes, green dyes, blue dyes, and any dyes with visible excitation and emission.

According to various embodiments, the concentration of DNA in a sample at a particular stage of PCR can be obtained by filtering light from the light source to permit only the wavelengths close to the peak excitation wavelength to impinge the sample. Further improvement can be achieved by filtering the light emitted from the sample so that only wavelengths close to the peak emission wavelength of a particular dye reach the detector.

Figure 3A:
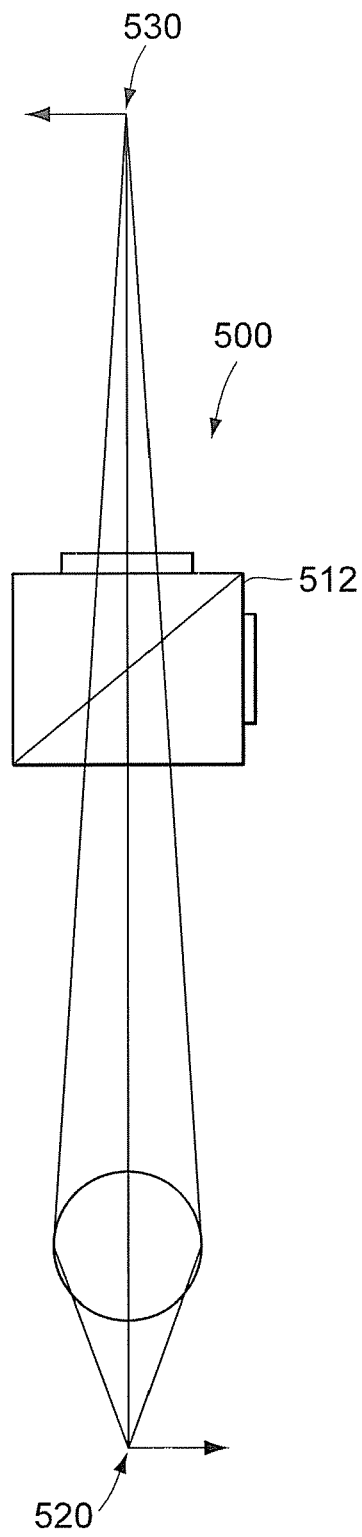
FIG. 3A is an optical imaging illustration of a microscopy system.

Microscopy systems are limited to monitoring DNA features of interest. For example, FIG. 3A shows a representative depiction 500 of the optical imaging of a microscopy system. The microscopy system uses a cube 512 to spectrally distinguish the fluorescent light. The light traversing the cube 512 must be in focus so that the light from sample 530 can be imaged on the detector 520. This allows the light emitted from the sample to consist of information about the spatial content of the sample in focus plane. While microscopy systems can resolve the spatial content of a sample, they are ill-suited for maximizing the transfer of energy from the sample to the detector and optimizing the collection of light.

Figure 3B:
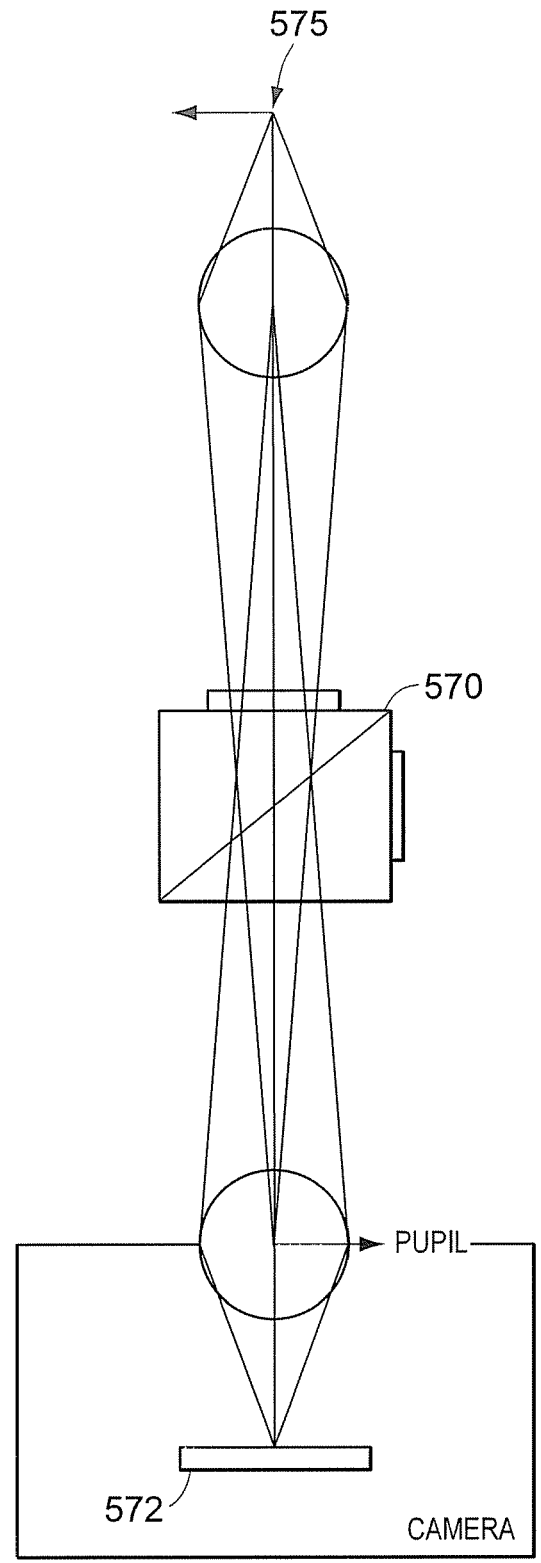
FIG. 3B is an optical imaging illustration of a fluorometry system.

According to various embodiments, fluorometry systems that use the optical arrangements described herein can measure the concentration of DNA in a sample at a particular stage of PCR. Fluorometry systems can image the sample into the pupil of the detector to provide an increase transfer of energy from the sample to the detector to better collect the light. FIG. 3B shows a representative depiction an optical detection of a fluorometry system. The fluorometry system uses, for example, an optical device 570 to spectrally distinguish the fluorescent light from sample 575, such as a dye mixed with DNA in an aqueous solution taking advantage of telecentric or Kuehler illumination. The emitted fluorescent light is directed through the optical device 570 and captured by the detector 572 is not in focus at the detector. Instead the light is in focus at the pupil of the detector. The light reaching the detector in a single measurement includes information about the concentration of spectrally distinguishable species in the volume of the sample 575.

According to various embodiments, the present teachings can include different lens arrangements that can mitigate spatial illumination non-uniformity and/or spatial collection non-uniformity. Non-uniformity can be due to the dependence of filtration characteristics on angle of incidence and the cosine$^4$ law. Another source of non-uniformity can be from vignetting. Further, the non-uniformity of flux can be dependent on wavelength. The present teaching can also mitigate the need for the spectra of each dye to be collected for every well during instrument calibration. Additionally, the present teaching can mitigate the need for a passive internal reference dye to normalize a portion of the spatial non-uniformity. For example, FIG. 2B shows a representative depiction 430 of a lens arrangement that includes beamsplitter 445, excitation filter 450, and emission filter 460. As shown in FIG. 2B, the light rays converge as they impinge any of the beamsplitter 445, excitation filter 450 or emission filter 460. FIG. 2B illustrates a system where the light passing through the optical device is non-collimated.

According to various embodiments, the present teaching can include positive and/or negative lenses. FIG. 2C shows a representative depiction 475 of a lens arrangement that includes beamsplitter 445, excitation filter 450, emission filter 460, a negative lens 470, and at least one positive lens, such as positive lens 480a and/or 480b. Positive lens 480a can be positioned to receive and collimate light emitted from the sample region and direct the collimated light to impinge on beamsplitter 445. Additionally, positive lens 480b can be positioned to receive and collimate light emitted from the light source and direct the collimated light to impinge on beamsplitter 445. In various embodiments, a filter and a positive lens can be housed in a telescope element. For example, the excitation filter 450 and the positive lens 480b can be housed in a telescope element and/or the emission filter 460 and the positive lens 480b can be housed in a telescope element. In one example, the telescope element can be Fresnel lenses. In various embodiments, positive lens 480b can be excluded if a parabolic or collimating reflector is used with the light source.

According to various embodiments, the present teachings can provide multiple optical devices, where each optical device includes a specific beamsplitter and a specific set of filters, such as excitation and emission filters to provide an accurate measure of the concentration of DNA in a sample at various stages of PCR. The excitation filter in the set of filters can be chosen to allow wavelengths of light received from the light source that are close to the peak excitation wavelength of a predetermined dye to pass. The excitation filter can also be configured to block wavelengths of light that are greater than and/or less than the excitation wavelength. Similarly, the emission filter in the set of filters can be chosen to allow light close to the peak emission wavelength to pass while also blocking wavelengths outside the specific passband.

According to various embodiments, the present teachings can provide unique optical devices for each dye. This allows better sensitivity than if only one optical device is used for multiple dyes. Unique optical devices for each dye allows the excitation and emission wavelengths to be closer together than if a common optical device is used for all dyes. For example, unique excitation and emission filters for each dye allow the wavelengths of the excitation beam and emission beam to be better matched to the separated peak excitation and peak emission wavelengths of that dye than would be possible if a common excitation filter was shared across multiple emission filters. The closer the wavelength of light of the excitation beam to the peak excitation wavelength of the sample, the greater the intensity of the fluorescence emission. A single excitation wavelength band will not efficiently excite an entire set of dyes with excitation peaks spread through a range of wavelengths that is much larger than the single excitation peaks wavelength band because of the fixed, distinct separation between the peak excitation and peak emission wavelength for each dye. For example, blue excitation more efficiently excites dyes with blue peak excitation wavelengths, and less efficiently excites dyes with red peak excitation wavelengths. The closer the separation between the excitation band and the emission band is to the gap between the peak excitation and peak emission wavelengths (Stoke's shift), the greater the fluorescent emission. Higher emission intensity permits smaller concentrations of fluorescent material to be detected, and thus, the device can have an improved overall sensitivity. Further, using a beamsplitter that is unique to each optical device, such as beamsplitter of optical device, can add additional filtering of light at both the excitation and emission wavelengths and reduce unwanted noise at the wrong wavelength. Further, using unique excitation and/or emission filters close to the peak excitation and/or emission wavelengths separately or in combination with the light blocker reduces the errors that can result from temperature changes.

According to various embodiments, as illustrated in FIG. 1, fluorometry device 100 can include a light source 105, optical devices 110, a movable platform 115, a sample region 120, a detector 125, a focusing lens 130, a light blocker 135, and a motor 140. One example of the general arrangement of these components will now be described.

Light source 105 emits a source beam 107 that is received by one of the optical devices 110. For ease of illustration, FIG. 1 shows one optical device on movable platform 115. However, any number of optical devices can be installed on movable platform 115. A motor 140 is also attached to movable platform 115 with a stem 145. Motor 140 is used to move the movable platform 115 to interpose one of the optical devices 110 into the path of the source beam 107. The motor 140 can also move the movable platform 115 to interpose the light blocker 135 to prevent the source beam 107 from reaching the sample region 120.

The optical device 110 receives the source beam 107 and directs a portion as an excitation beam 121 through the focusing lens 130 to the sample region 120, where it impinges an array of samples 122. The excitation beam 121 causes one or more dyes in the samples 122 to fluoresce and emit light in the form of an emission beam 123.

The emission beam 123 is received by the optical device 110 and then directed by the optical device 110 to a detector 125. The detector 125 generates a data signal that includes information that is representative of the concentration of DNA in the samples 122.

According to various embodiments, the light source can be LEDs used to provide illumination wavelength uniformity, light power output uniformity, and minimal degradation of output over extended periods of time. Further, LEDs operate at relatively low temperatures and require little or no external cooling. In some embodiments, the size of the light emitted from the light source 105 can be adjusted to be as small as possible to maximize the energy density directed onto the samples 122.

Figure 2A:
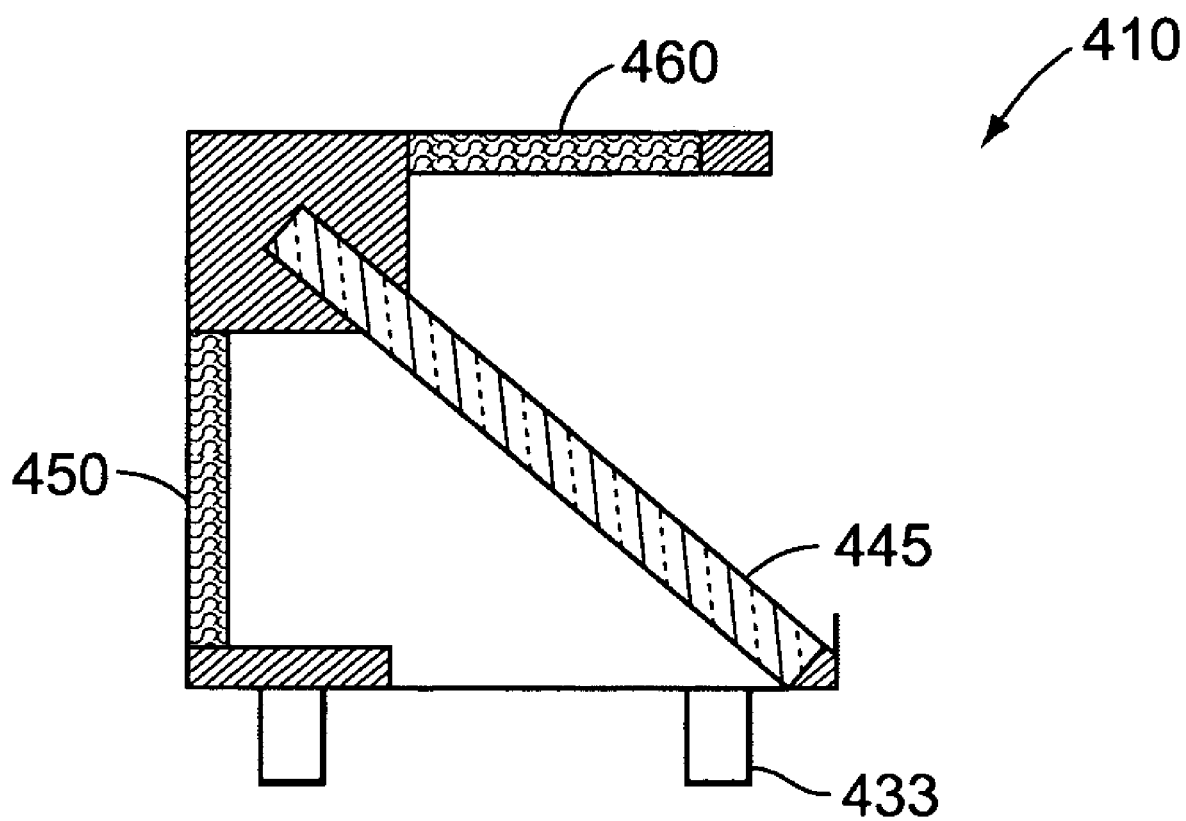
FIGS. 2A-2C illustrates representative optical devices according to various embodiments of the present teachings.
Figure 2B:
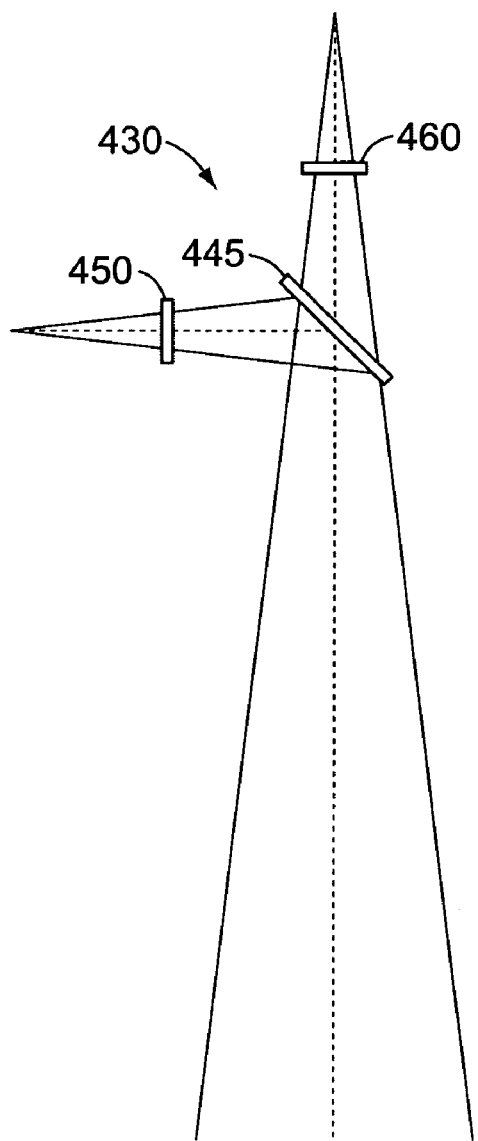
Figure 2C:
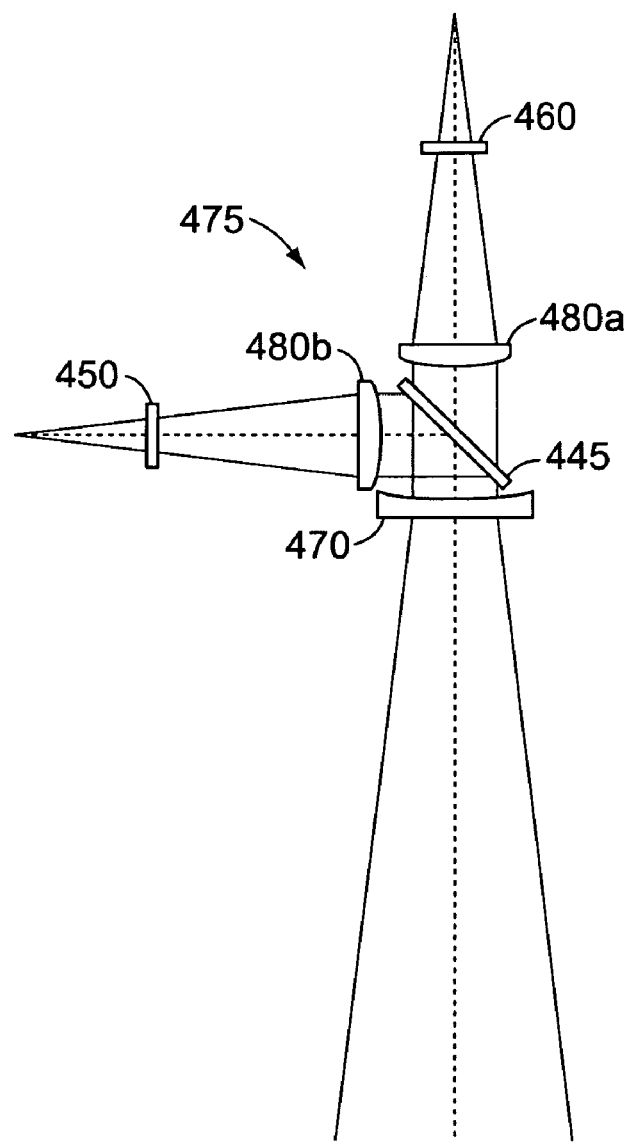

According to various embodiments, as illustrated in FIG. 2A, optical device 410 can include alignment pins 433, a beamsplitter 445, an excitation filter 450, and an emission filter 460.

According to various embodiments, alignment pins 433 ensure that optical device 410 can be precisely installed onto the movable platform 115, and thus, allow device 100 to easily interchange optical devices 110. Different optical devices can be removed and replaced through an access hatch in the instrument case (not shown) for device 100. For example, in some embodiments, one or more of the optical devices 110 attached to the movable platform can be tailored to measure the concentration of DNA based on particular dyes. However, if other dyes are used, alignment pins 433 allow device 100 to easily use other optical device that are tailored to these other dyes. An optical device 110 can be removed from the movable platform 115; and a new optical device, such as optical device 410, can then be installed onto movable platform 115 using alignment pins 433 to ensure proper positioning.

The process of aligning optical device 410 can include positioning the alignment pins 433 into one or more sets of holes (not shown in FIG. 1) in movable platform 115. In order to confirm that optical device 410 is properly positioned, a fluorescent target that has known characteristic excitation and emission wavelengths, such as a dye exposed to DNA, can be placed in the sample region 120. The optical device 410 and/or the movable platform 115 can then be moved, for example in small increments, such that the detector 125 detects the maximum amount of light emitted from the fluorescent target. The position of the optical device 410 and/or the movable platform 115 is then recorded. This process can be repeated for any combination of optical devices and fluorescent targets. Alternatively, the optical device 410 can be aligned using a reference mirror (not shown) and one or more auto-collimators.

Accordingly, alignment pins 433 assist in installing and aligning optical devices 110 in device 100. Prior devices required continual re-alignment and disassembly of the device. These prior devices also required mechanical gauges or special tools to align the optical device and to re-assemble the device. In contrast, the optimal alignment position for each optical device 110 can be known using alignment pins 433 and the optical devices 110 can be easily and quickly substituted without requiring re-alignment.

According to various embodiments, excitation filter 450 can be used to selectively pass one or more wavelengths of source beam 107. The excitation filter 450 can be mounted in optical device 410. The wavelengths passed by the excitation filter 450 can be chosen to block wavelengths shorter and/or longer than the passband matched to the peak excitation wavelength of a particular dye exposed to DNA at a particular stage in PCR. In some embodiments, the excitation filter 450 can block wavelengths less than 400-475 nanometers and greater than 475-525 nanometers shorter and/or longer than the excitation wavelength of a particular dye exposed to DNA at a particular stage in PCR. Accordingly, the excitation filter 450 can ensure that the excitation beam 121 will be close to the characteristic excitation wavelength of a particular dye without having significant overlap with the excitation spectra of a different dye in the sample.

According to various embodiments, optical device 410 can include an emission filter 460. The emission filter 460 can be disposed in optical device 410 to receive the emission beam 123 before it reaches the detector 125. The emission filter 460 can be configured to block light having the wavelengths that lie within the excitation filter passband of a particular dye exposed to DNA at a particular stage in PCR and allow wavelengths around the emission wavelength and/or longer to pass. Accordingly, the emission filter 460 can ensure that the emission beam 123 reaching the detector 125 will be close to the characteristic emission wavelength of the dye.

According to various embodiments, beamsplitter 445 can be a dichroic or non-dichroic reflector positioned at 45 degrees. However, depending on the application, the beamsplitter 445 can be positioned at angles other than 45 degrees. According to various embodiments, beamsplitter 445 can be chosen to transmit wavelengths of light that are longer than the passband of the excitation filter of a particular dye exposed to DNA at a particular stage of PCR. The beamsplitter 445 can also be chosen to transmit wavelengths that are at, or shorter than, the passband of the excitation filter of a particular dye exposed to DNA at a particular stage of PCR. For example, the beamsplitter 445 can reflect wavelengths that are less than 450-500 nanometers shorter than the characteristic wavelength. According to various embodiments, beamsplitter 445 can be a 50-50 partly silvered mirror.

Figure 4A:
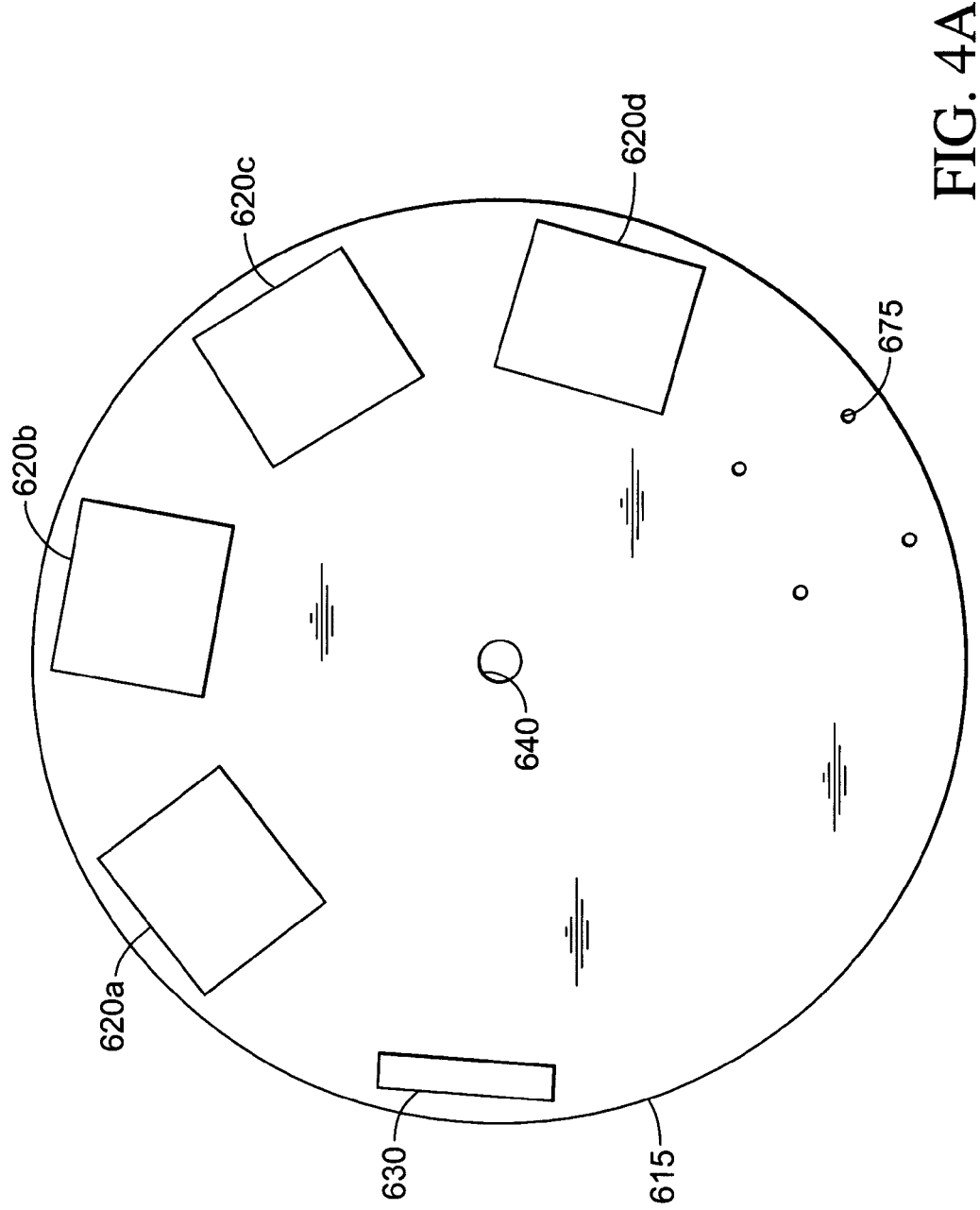
FIG. 4A illustrates a representative movable platform according to various embodiments of the present teachings.
Figure 4B:
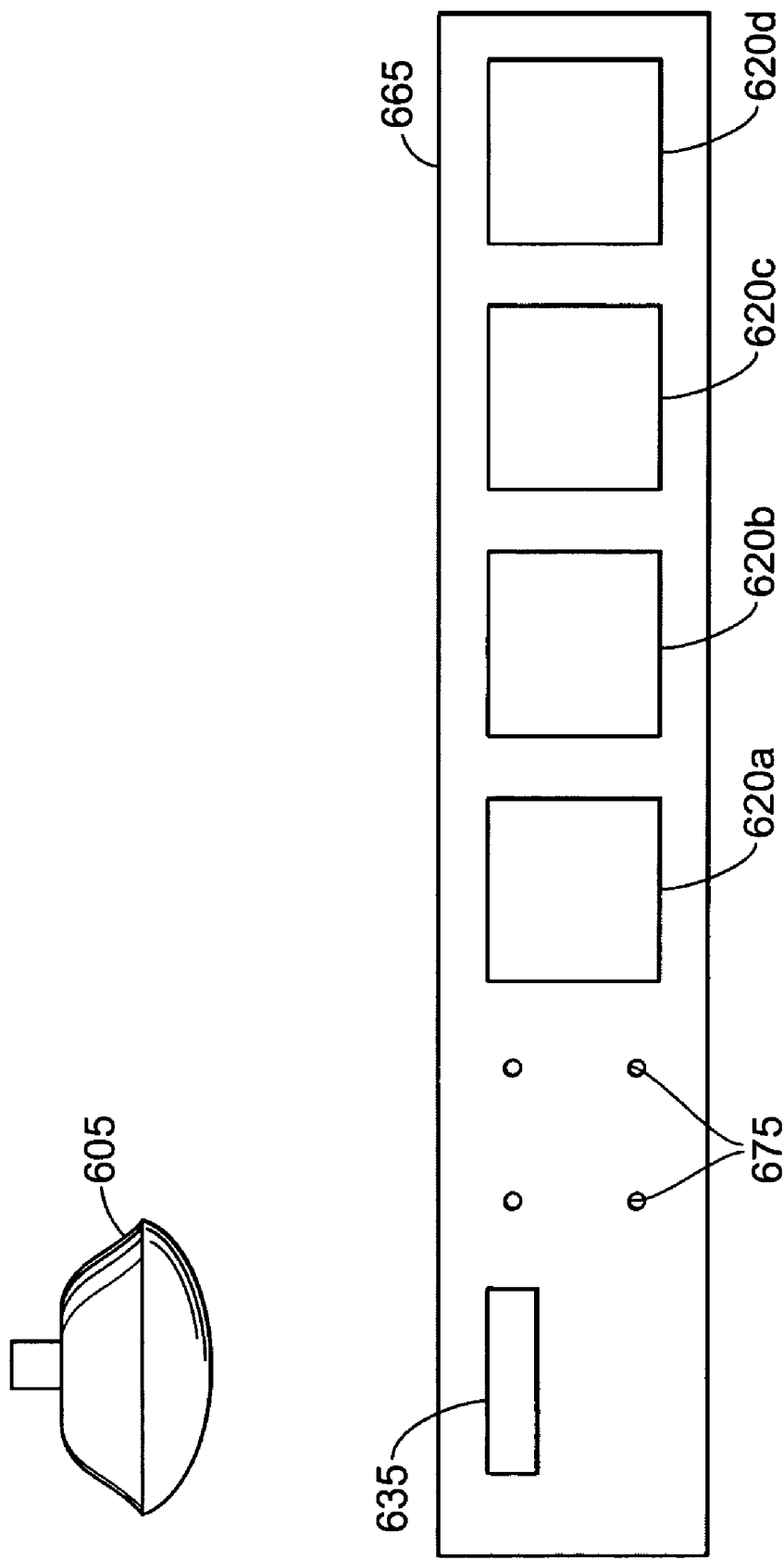
FIG. 4B illustrates a representative movable platform according to various embodiments of the present teachings.

According to various embodiments, as illustrated in FIGS. 4A and 4B. movable platforms can be configured to provide circular and/or lateral movement. FIG. 4A depicts a rotatable movable platform 615 such as a turret or carrousel assembly. Rotatable movable platform 615 can be rotated to move the different optical devices 620a, 620b, 620c, and 620d to receive light from the light source 605 (not shown in FIG. 4A) and to position light blocker 630 to block light from reaching the sample. The rotatable movable platform 615 can be generally circular, or any portion of a circle, so long as it can be rotated and can accommodate multiple attachments. For example, the rotatable movable platform 615 can accommodate multiple optical devices and a light blocker and can be rotated to position these attachments to receive light from the light source 605.

FIG. 4B depicts a linearly movable platform 665. Linearly movable platform 665 can be moved linearly to position different optical devices 620a, 620b, 620c, and 620d to receive light from the light source 605 and to position light blocker 635 to block light from reaching the sample. The linearly movable platform 665 can be any shape, such as rectangular, so long as it can accommodate multiple attachments and can be moved linearly to position the attachments to receive light from the light source 605.

According to various embodiments, movable platforms 615 and 665 can also include precision alignment pinholes 675, which are designed to receive alignment pins of an attachment, such as alignment pins 433 of optical device 410. As shown in FIGS. 4A and 4B, the precision alignment pinholes 675 can be holes formed in the movable platforms 615 and 665 and receive the precision alignment pins of the optical devices 620a-620d and the light blocker 635.

Now referring back to FIG. 1, sample region 120 provides a location for holding one or more of the samples 122. For example, sample region 120 can be structured as a tray or bracket that holds one or more vials of the sample 122.

Sample 122 can be an aqueous suspension of ingredients used for holding one or more "seed" samples of DNA. The aqueous suspension of sample 122 include selected DNA primer strands, DNA elements, enzymes, and other chemicals. During the PCR process, the sample 122 is thermally cycled, which causes the DNA sample to replicate itself.

According to various embodiments, detector 125 detects light, such as emission beam 123, emitted from the sample 122. According to various embodiments, detector 125 generates a signal indicating the amount or concentration of DNA present in sample 122 based on the light emitted from sample 122. For example, detector 125 can include one or more processing devices to generate the signal. According to various embodiments, detector 125 can be connected to a processing device that generates the signal.

According to various embodiments, lens 130 can be optionally included in device 100 to assist in focusing light, such as the excitation beam 107, onto sample region 120. Lens 130 can be constructed from known materials and have various refractory properties to focus light onto sample region 120. For example, some embodiments of the invention use a Fresnel lens for the lens 130.

According to various embodiments, light blocker 135 allows the device 100 to control when sample region is illuminated by the light source 105. Light blocker 135 can be useful because some dyes become spectrally unstable when they are exposed to changes in temperature, such as from the light source or from PCR. In particular, the peak excitation and emission wavelengths of a dye can "drift" or weaken when the dye is exposed to temperature changes. In prior devices, the light source required a warm-up time to stabilize. During this stabilization period, it is possible to photobleach the sample. Photobleaching weakens the emission spectrum from the dye and can result in the degradation of the signal causing the detector to sense an incorrect concentration of DNA.

According to various embodiments, light blocker 135 can be used in device 100 to allow light source 105 to be on continuously. Rather than using a separate mechanical or electronic shutter, device 100 can include a light blocker 135, such as a blocking plate, that is attached to the movable platform 115. Accordingly, the motor 140 can also be used to position the movable platform 115, such that the light blocker 135 is blocks light from the light source 135.

According to various embodiments, motor 140 moves movable platform 115 into various positions to interpose optical devices 110 into the path of source beam 107. As shown in FIG. 1, motor 140 can be a direct-drive stepper motor. According to various embodiments, as illustrated in FIG. 4A, motor 140 that can be attached to movable platform 115 by the stem 145 that is mounted into a mounting hole 640. During operation, motor 140 rotates the rotatable movable platform 615 to position different optical devices 620a-620d or the light blocker 635 into and out of the optical path of the source beam.

According to various embodiments, motor 140 can be any motor that provides linear movement. For example, as shown in FIG. 4B, motor 140 can linearly move movable platform 665. For ease of illustration, the embodiments shown in FIGS. 4A and 4B include four optical devices. However, some embodiments of movable platforms 115, 615, and 665 can accommodate any number of optical devices.

Figure 5:
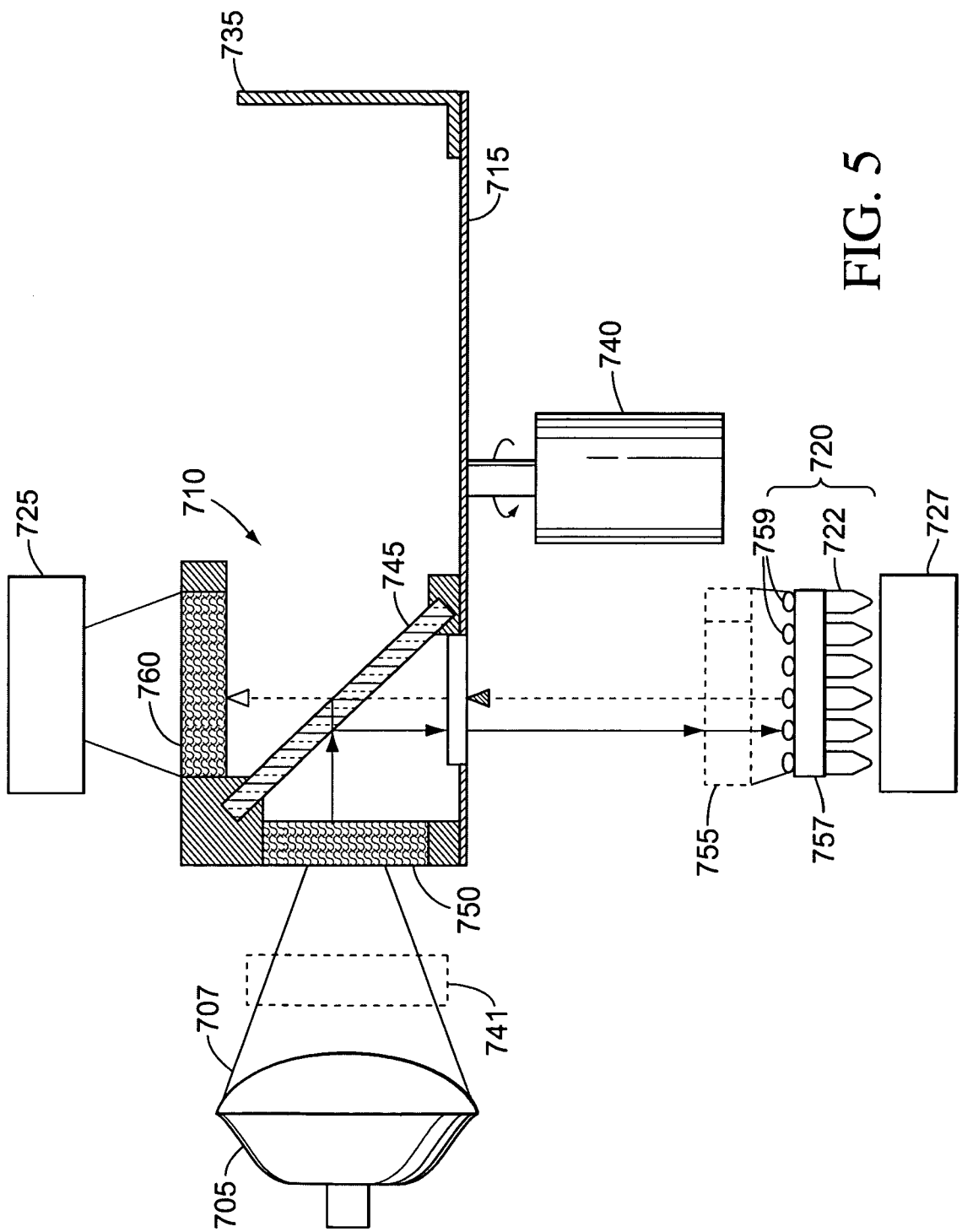
FIG. 5 illustrates the operation of a representative fluorometry system according to various embodiments of the present teachings.

According to various embodiments, the operation of device 100 will now be described with reference to FIG. 5. As shown in FIG. 5, some embodiments of the invention operate by allowing the light source 705, such as an illumination lamp or LED, to warm to a steady state temperature. The motor 740 positions the light blocker 735 attached to the movable platform 715 to block the source beam 707 from reaching the sample region 720. The light blocker 735 can be positioned in front of source beam 707 before the light source 705 is turned on or before the sample 722 is placed in the sample region 720. The sample 722 is then temperature cycled, using the temperature controller 727 to initiate the PCR process. At the appropriate time of interest during PCR, the motor 740 moves the movable platform 715 to position the first of a plurality of optical devices 710 to receive the source beam 707. An infra-red (IR) hot mirror filter 741 optionally can be placed between the light source 705 and the optical device 710.

The source beam 707 goes through the IR hot mirror filter 741 and is received by the excitation filter 750. The source beam reflects off of the beamsplitter 745 and is directed to the sample region 720. A Fresnel lens 755 optionally can be placed between the beamsplitter 745 and the sample region 720. Additionally, the multiple samples can be held in a sample holder 757 that optionally can include well lenses 759 positioned above each sample 722. The Fresnel lens 755 and the well lenses 759 act to focus the light onto the sample 722. Wavelengths of light emitted by the light source 705 that are shorter and/or longer than the excitation wavelength of the particular dye exposed to DNA at the appropriate time of PCR are blocked by the excitation filter 750 and/or transmit through the beamsplitter 745. Light that impinges the sample 722 is shown as a solid line in FIG. 5 with solid arrowheads and can be referred to as the excitation beam.

The excitation beam then causes dyes exposed to DNA in the sample 722 to emit or fluoresce light. Light emitted from the sample 722, shown as a broken line with hatched arrowheads in FIG. 5, transmits through the well lens 759, the Fresnel lens 755, the beamsplitter 745, and the emission filter 760. Undesired wavelengths of light emitted from the sample 722 are reflected by the beamsplitter 745 or are blocked by the emission filter 760. The portion of the emitted light that transmits through the beamsplitter 745 and emission filter 760 is received by the detector 725, such as a camera or CCD camera. This transmitted light is shown with a broken line with non-shaded arrowheads in FIG. 5 and can be referred to as the emission beam.

According to various embodiments, sample holder 757 that holds the sample 722 can include vials typically formed conically in a plastic unitary tray. The plastic tray can contain a plurality of vials, for example 96 vials in an array of 12 by 8, to hold multiple samples. The tray can be removed from the system for sample preparation. A plastic unitary cover with caps for the vials can rest on or attach to the vials to prevent contamination or evaporation loss. Other systems can be used for this function, such as oil on the top of the sample surface, in which case caps are not needed. If caps are used, they can be transparent to light used by the instrument and can be convex facing upwardly from the sample. A platen (not shown) can optionally rest over the vial caps or, if no caps are used, then directly over the vials. The platen, which can be made of metal, can have an array of holes aligned with the vials. Each hole can have a diameter about the same diameter as the vial top diameter. If there are caps, the platen can have its temperature maintained by a film heater or other device to heat the platen. Heating the platen helps to prevent condensation under the caps without interfering with DNA replication in the vials. For example, the platen can be held at a temperature slightly higher than the highest sample temperature that the thermal cycle reaches.

According to various embodiments, the present teachings provide impinging the excitation beam on sample holder 757 and generating a fluorescent signal from the plurality of samples 722. This permits the detector 725 to generate a data signal representative of the concentration of DNA in the samples at the particular stage of PCR.

At the next appropriate time of interest in PCR, after the detector 725 generates the data signal that results from the first optical device 710 receiving the source beam 707, the motor 740 moves the movable platform 715 to position another one of the plurality of optical devices 710 (not shown) to receive the source beam 707. The other one of the plurality of optical devices receives the source beam 707 and the process detailed above is repeated. The above processes can be repeated for each appropriate time of interest in PCR.

After the dye colors of interest are measured, the movable platform 715 can be moved to position the light blocker 735 to block the source beam 707. The samples 722 can then be temperature cycled to prepare them for the next detection or until all desired detection has been completed.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A fluorometry device for determining concentration of spectrally distinguishable species in a biological sample, the device comprising:
   a light source adapted to provide a source beam;
   a plurality of samples;
   a plurality of optical devices adapted to filter the source beam, to filter fluorescent light from the samples, and to separate the source beam from the fluorescent light, wherein each of the plurality of optical devices is coupled to a movable platform; and
   a detector adapted to receive the fluorescent light emitted from the samples, wherein the fluorescent light is not in focus and does not provide spatial content from a focus plane in the samples,
   wherein the device provides a data signal representative of the concentration of spectrally distinguishable species based on the intensity of fluorescent light emitted by the samples.

2. The fluorometry device of claim 1, further comprising:
   a beamsplitter adapted to separate the source beam from the fluorescent light.

3. The fluorometry device of claim 2, further comprising:
   an excitation filter adapted to filter the source beam and an emission filter adapted to filter the fluorescent light, wherein the excitation filter, the emission filter, and the beamsplitter provide a first narrow wavelength range for excitation and a second narrow wavelength range for emission.

4. The fluorometry device of claim 1, further comprising:
   a motor adapted to move the platform to align the source beam with each optical device and to align the samples with the detector.

5. The fluorometry device of claim 4, wherein the motor rotates the platform.

6. The fluorometry device of claim 4, wherein the motor linearly moves the platform.

7. The fluorometry device of claim 1, further comprising:
   a light blocker attached to the movable platform adapted to prevent the source beam from reaching the samples.

8. The fluorometry device of claim 1, further comprising:
   an alignment pin connected to the optical device.

9. The fluorometry device of claim 1, wherein the light source comprises at least one LED.

10. The fluorometry device of claim 1, wherein the optical device collimates the light passing through it.

11. A method of determining the concentration of spectrally distinguishable species in a biological sample with fluorometry, the method comprising:
    moving a movable platform to position a first optical device in the optical paths between a light source and a plurality of samples and between the sample region and a detector;
    passing light from the light source to the sample region and from the sample region to the detector through the first optical device, wherein the first optical device passes light in a first wavelength band that primarily excites a first dye from the light source to the sample region, and passes light in a second wavelength band that is primarily emitted from the first dye from sample region to the detector;
    moving the movable platform to position a second optical device in the optical paths between the light source and the sample region and between the sample region and the detector;
    passing light from the light source to sample region and from the sample region to the detector through the second optical device, wherein the second optical device passes light in a third wavelength band that primarily excites a second dye from the light source to the sample region, and passes light in a fourth wavelength band that is primarily emitted from of the second dye from the sample region to the detector;
    focusing the light in the second wavelength band and fourth wavelength band on a pupil of a camera; and
    generating a data signal representative of the concentration of the spectrally distinguishable species in the sample based on the light passed from the sample region to the detector.

12. The method of claim 11, further comprising:
    moving the movable platform to interpose a light blocker to prevent a substantial portion of light from reaching the sample region.

13. The method of claim 12, wherein the optical devices and the light blocker are moved by rotating the movable platform.

14. The method of claim 12, wherein the optical devices and the light blocker are moved by linearly moving the movable platform.

15. A method of determining the concentration of spectrally distinguishable species in a biological sample with fluorometry, the method comprising:
    providing a plurality of samples comprising a plurality of spectrally distinguishable species;

providing a plurality of optical devices adapted to filter excitation light, to filter fluorescent light from the samples, and to separate the excitation light from the fluorescent light, wherein each of the plurality of optical devices is coupled to a movable platform, and wherein each optical device is adapted to one spectrally distinguishable species in the samples;

focusing the light in a second wavelength band and a fourth wavelength band on a pupil of a camera;

thermal cycling the plurality of samples;

transitioning between optical device by moving the platform;

determining the concentration of each spectrally distinguishable species by using a data signal generated throughout the thermal cycling.

16. The method of claim 15, wherein the concentration of spectrally distinguishable species provides information related to a diagnostic assay.

17. The method of claim 16, wherein the diagnostic assay is for HIV screening.

18. An apparatus for determining the concentration of spectrally distinguishable species in a biological sample by fluorometry, the device comprising:

means for moving each one of a plurality of optical devices disposed on a platform to receive a source beam directed towards a sample and emitted from a light source;

means for blocking a plurality of wavelengths of light in the source beam;

means for blocking a plurality of wavelengths of light emitted from the sample when the sample comprises DNA and at least one dye; and means for generating a plurality of data signals, each data signal representative of the concentration of DNA in the sample, wherein a data signal is generated when each one of the plurality of optical devices receives the source beam.

* * * * *